US00PP33295P2

(12) United States Plant Patent
Hansen

(10) Patent No.: US PP33,295 P2
(45) Date of Patent: Jul. 27, 2021

(54) ***PHLOX* PLANT NAMED 'OPALESCENCE'**

(50) Latin Name: *Phlox paniculata*
Varietal Denomination: Opalescence

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/974,229

(22) Filed: Nov. 19, 2020

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
CPC ... A01H 5/02; A01H 5/00; A01H 6/70; A01H 6/36
See application file for complete search history.

(56) References Cited

PUBLICATIONS

Digger Magazine Farwest New Varieties Showcase 2020, retrieved on Mar. 15, 2021, retrieved from the Internet at http://www.diggermagazine.com/wp-content/uploads/2020/08/New-Varieties-2020-Final.pdf, pp. 34-48. (Year: 2020).*
Hawke Plant Evaluation Notes An Evaluation Report of Selected *Phlox* Species and Hybrids, Chicago Botanic Garden, RE9095 Issue 13, 1999, 1-4. (Year: 1999).*

* cited by examiner

*Primary Examiner* — June Hwu

(57) ABSTRACT

A unique cultivar of Tall *Phlox* named 'Opalescence' characterized by vigorous, dense, upright, multi-stemmed, winter-hardy habit with dark-green, lanceolate leaves. Flowering begins in late-July and continuing for up to five weeks in cooler weather conditions, on heavily-branched peduncles and completely cover the top of the plant in peak season. Petals are light pink with darker pink eye. The new plant is able to withstand dry conditions once established, and the foliage stays clean and resists mildew. The new plant shows excellent powdery mildew resistance. The new plant is especially suitable for a cut flower, for the landscape as a potted plant and in the garden as a specimen or en masse.

1 Drawing Sheet

Botanical classification: *Phlox paniculata.*
Variety denomination: 'Opalescence'.

STATEMENT REGARDING PRIOR DISCLOSURES UNDER 37 CFR 1.77(b)(6)

The first non-enabling disclosure of the claimed plant, in the form of a photograph and brief description on a website operated by Walters Gardens, Inc. on Dec. 1, 2019. Subsequently, the new plant was advertised in the "Walters Gardens 20-21 Catalog" by Walters Gardens, Inc. released on May 20, 2020. The claimed plant was first sold to Ivy Acres, Inc. on Feb. 24, 2020 by Walters Gardens, Inc., who obtained the plant and all information relating thereto, from the inventor. No plants of *Phlox* 'Opalescence' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Tall *Phlox* plant known as *Phlox* 'Opalescence' and will be referred to hereafter by its cultivar name, 'Opalescence', or the "new plant". The new plant was hybridized by the inventor at a wholesale perennial nursery in Zeeland, Mich. between *Phlox paniculata* 'Rosalinda' (not patented) as the female or seed parent and *Phlox paniculata* 'Dodo Hanbury Forbes' (not patented) as the male or pollen parent. The new plant passed initial evaluation on the summer of 2016 and was assigned the breeder code 14-591-1 through the remaining evaluation process. 'Opalescence' was first asexually propagated by division in the fall of 2016 followed by shoot tip cuttings in the greenhouses at the same nursery in Zeeland, Mich. in the summer of 2017. The unique characteristics of the new plant have been found to be reproducible and stable in successive generations of asexually propagated and the resultant plants have been found to be identical to the original selection.

BRIEF SUMMARY OF THE PLANT

*Phlox* 'Opalescence' is unique from all other Tall *Phlox* known to the inventor. The nearest comparison plants known to the inventor include: the female and male parents, 'Uptown Girl' U.S. Plant Pat. No. 32,287, 'Bright Eyes' (not patented), 'Balkapowibi' U.S. Plant Pat. No. 30,782, 'and 'Swizzle' U.S. Plant Pat. No. 19,813. The female parent, 'Rosalinda', has a taller habit and slightly deeper pink flowers with less obvious eye. 'Dodo Hanbury Forbes' has a taller habit with flowers of deeper pink. 'Uptown Girl' has a similar habit with slightly lighter green foliage and flowers of slightly lighter pink. 'Bright Eyes' has a taller habit with lighter green foliage and the flowers are more cupped and not as flat. 'Balkapowibi' has a shorter habit and the flower petals are lighter pink with a darker red eye. 'Swizzle' has a shorter habit and more pink flowers that fade more to whiter petal faces.

*Phlox* 'Opalescence' differs from and all other *Phlox* known to the inventor in the following repeatedly observed traits in combination:

1. Vigorous plants of dense upright habit, producing clean, dark-green, lanceolate leaves;
2. Multiple stems produce large branched panicles;
3. Flower beginning in late-July and continuing for up to five weeks completely covering top of plant at peak flowering;
4. Flowers of light pink with dark pink eye;
5. Excellent powdery mildew resistance.

BRIEF DESCRIPTION OF THE DRAWINGS

The photographs of the new plant demonstrate the unique traits of *Phlox* 'Opalescence' and the overall appearance of the plant at three-years-old growing in a full-sun trial garden in Zeeland, Mich. The colors in the drawings are as accurate as reasonably possible with color reproductions. Variation in ambient light spectrum, source and direction may cause the appearance of minor variation in color.

DETAILED BOTANICAL DESCRIPTION

Figure 1:
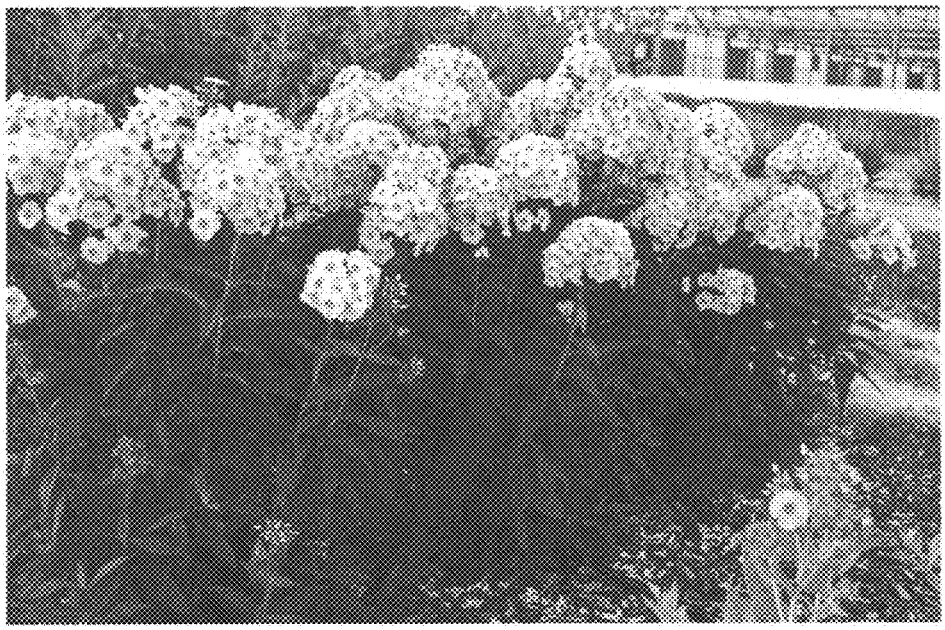
FIG. 1 shows a landscape habit view of the new plant in peak flower.
Figure 2:
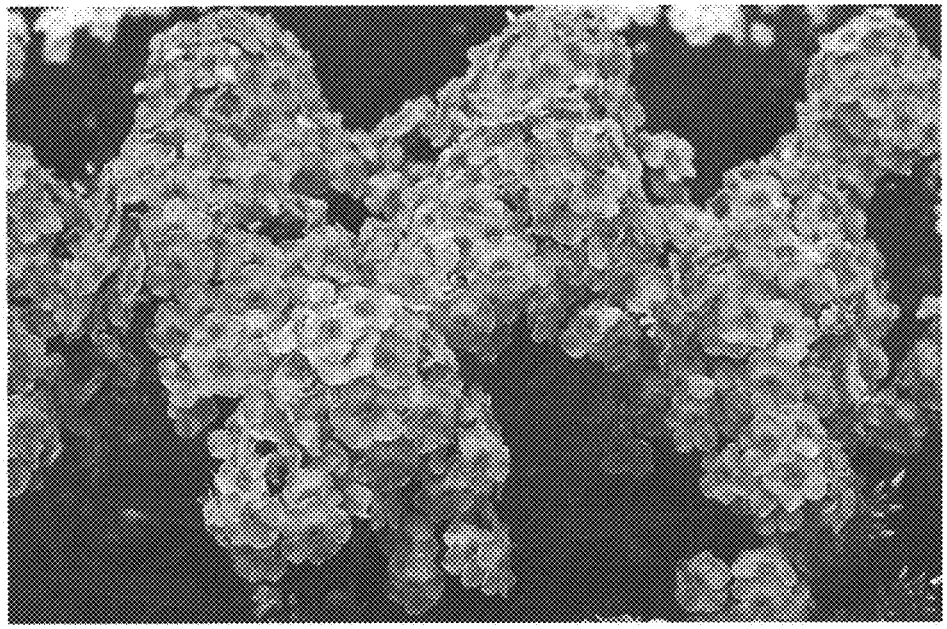
FIG. 2 shows a close-up of the flowers.

The following descriptions and color references are based on the 2015 edition of The Royal Horticultural Society Colour Chart except where common dictionary terms are used. *Phlox* 'Opalescence' has not been observed under all possible environments. The phenotype may vary slightly with different growing environments such as temperature, light, fertility, soil pH, moisture and maturity levels, but without any change in the genotype. The following observations and size descriptions are based on two-year-old plants in a partially shaded greenhouse or a full-sun trial garden of a wholesale perennial nursery in Zeeland, Mich. with supplemental fertilizer and water as needed.

Botanical classification: *Phlox paniculata;*

Parentage: Female or seed parent is *Phlox paniculata* 'Rosalinda'; the male or pollen parent is *Phlox paniculata* 'Dodo Hanbury Forbes';

Plant habit: Winter-hardy, evergreen herbaceous perennial; dense, producing about 15 stiff, upright stems; flowering to about 66.0 cm tall and 54.0 cm wide;

Propagation: Stem cuttings; rooting in about 3 weeks;

Time to produce finished crop in 3.8 liter pots: About 8 to 10 weeks; vigorous;

Root: Fibrous and freely branching; color creamy white to tan depending on soil type;

Leaves: Simple; opposite; lanceolate; apex narrowly acute; base attenuate, clasping; margin micro-ciliolate; glabrous both adaxial and abaxial; to about 15.5 cm long by about 4.8 cm wide, average about 13.8 cm long and 4.2 cm wide;

Leaf color: Adaxial expanding between RHS 146A and RHS 144A and abaxial expanding between RHS 147C and RHS 146C; mature adaxial nearest RHS NN137B and mature abaxial between RHS 137C and RHS 138A; lacking anthocyanin expression;

Foliage fragrance: None detected;

Veins: Pinnate; glabrous adaxial and abaxial, midrib about 1.5 mm wide at base; slightly impressed adaxial and costate abaxial;

Vein color: Adaxial midrib nearest RHS 145C and primary veins nearest RHS 148D; abaxial midrib nearest RHS 146D and primary veins nearest RHS 137A;

Petiole: Leaves sessile;

Stems: Cylindrical; stiff; upright; glabrous, limited branching below flowers; to about 32.0 cm long and 9.0 mm diameter near base;

Stem color: Nearest RHS 146D, developing ridges of nearest RHS 161A with maturity; lacking anthocyanin expression;

Nodes: 17 nodes before flowers; average about 1.9 cm apart proximally; distally less than 1.0 mm apart;

Node color: Color nearest RHS 146D;

Inflorescence: Upright; with 8 branched nodes; flowering in about the upper 34.0 cm and about 18.5 cm wide; average of 500 flowers;

Flowers: Perfect; salverform; mostly flat faced; about 38.0 mm across face and 25.0 mm long; with fused corolla tube about 22.0 mm long and 4.0 mm diameter near face and 3.0 mm diameter at base; attitude upright to outwardly;

Flower longevity: About 5 days on plant; self-cleaning;

Flower fragrance: Lightly sweet;

Buds one to two days prior to opening: Narrowly clavate; bluntly acute apex with rounded base; petals implicate; about 23.0 mm long, 12.0 mm long in terminal bulb portion and 11.0 mm long in tube; corolla tube to 3.5 mm diameter near face and 2.5 mm diameter at base, bulb to 5.0 mm diameter;

Bud color: Exposed petal bulb portion variable, nearest RHS 69A and RHS 75A; corolla tube portion variable, nearest RHS N77B and between RHS 72B and RHS N75D; calyx nearest RHS 146D with transparent margins and a light blush of nearest RHS 187B;

Petals: Five; consisting of limb and basal claw fused into corolla tube; limb obdeltoid to nearly orbicular; apex rounded, margin entire; limbs imbricate about 30 percent; glabrous adaxial and abaxial corolla tube puberulent;

Petal size: Limb about 17.0 mm long and 20.0 mm wide near middle; tube about 22.0 mm long and 4.0 mm diameter near face and 3.0 mm diameter near base;

Petal color upon first opening:

*Adaxial.*—Limb nearest RHS N75C, with center eye nearest RHS NN74A; proximal 3.0 mm of tube nearest RHS 145D, remaining distal tube portion lighter than RHS N77D.

*Abaxial.*—Limb between RHS 76C and RHS 76D, proximal 3.0 mm of tube nearest RHS 145D, remaining distal tube portion nearest RHS N77D.

Petal color upon maturity:

*Adaxial.*—Limb variable with nearest RHS 75B and RHS NN155D with central eye nearest RHS NN74A; proximal 2.0 mm of tube base nearest RHS 145C, remaining distal tube portion nearest RHS N77D.

*Abaxial.*—Limb nearest RHS 75D, proximal 3.0 mm of tube nearest RHS 145C, remaining distal tube portion nearest RHS N77D.

*Androecium.*—Typically five.

Filaments: Typically five, adnate to inner corolla to various heights about 11.0 mm to 19.0 mm from base; free in the distal 0.5 mm to 1.0 mm long and 0.2 mm in diameter; color nearest RHS NN155D;

Anther: Five; oblong elliptic; basifixed; longitudinal; oblong, about 3.5 mm long by 1.5 mm wide; color nearest RHS 11C;

Pollen: Nearly microscopic; color between RHS 11C and RHS 11B;

Gynoecium: One pistil per flower; 25.0 mm long;

Style: Cylindrical; about 19.0 mm long and 0.3 mm diameter when flower is mature; persistent after flower abscission; color proximally nearest RHS 145C and distally nearest RHS 145C with moderate blush of nearest RHS 182D;

Stigma: Trifid in proximal 2.0 mm long, about 0.2 mm diameter; color nearest RHS 4C;

Ovary: Inferior; conical; glabrous; lustrous; slightly acute apex and truncate base; about 3.0 mm long and 1.0 mm diameter; color nearest RHS 143A;

Calyx: Campanulate; about 11.5 mm long and 4.5 mm across at apex;

Sepals: Five; linear; adaxial slightly lustrous and matte abaxial; narrowly acute apex, fused in basal 4.5 mm, free in distal 7.0 mm; margin entire; individually about 11.5 mm long and 1.0 mm wide at fusion;

Sepal color: Adaxial nearest RHS 146B with light blush of nearest RHS 187B and transparent margin; abaxial nearest RHS 146D with light blush in high light exposure of nearest RHS 187B and a transparent margin;

Peduncle: Glabrous; stiff; upright; cylindrical; highly branched; to 34.0 cm long and 5.0 mm diameter; with up to 18 branches at about a 45 degree angle from horizontal, branches to about 2.5 mm diameter at base and 30.0 cm long;

Peduncle color: Nearest RHS 146C;

Pedicle: Cylindrical; micro-puberulent; flexible; upright to outwardly; to about 6.0 mm long and 1.0 mm diameter;

Pedicle color: Nearest RHS 146D with light blush of nearest RHS 187C;

Fruit: Dehiscent, few-seeded capsule, typically 1 with up to 3 seeds; fecundity low; globose; glabrous; to about 7.0 mm and 4.0 mm diameter; color at maturity nearest RHS 164A distally and nearest RHS 164C proximally;

Seeds: Flattened ellipsoidal; glabrous; to 5.0 mm long, 3.0 mm across and 1.5 mm thick; color nearest RHS 202A;

Hardiness and culture: The new plant grows best with full sun, light moisture and deep drainage; hardy to at least from USDA zone 3 through 8.

Disease and pest resistance: *Phlox* 'Opalescence' demonstrates excellent powdery mildew (*Erysiphe cichoracearum*) resistance under conditions that would normally show symptoms.

I claim:

1. A new and distinct cultivar of Tall *Phlox, Phlox* plant named 'Opalescence', as herein described and illustrated.

* * * * *